(12) United States Patent
Isogai et al.

(10) Patent No.: US 9,681,803 B2
(45) Date of Patent: *Jun. 20, 2017

(54) METHOD OF OBSERVING A THREE-DIMENSIONAL IMAGE OF EXAMINEE'S EYE

(71) Applicant: NIDEK CO., LTD., Gamagori-shi, Aichi (JP)

(72) Inventors: Naoki Isogai, Nishio (JP); Masaaki Hanebuchi, Nukata-gun (JP); Toshio Murata, Milpitas, CA (US)

(73) Assignee: NIDEK CO., LTD., Gamagori-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/811,336

(22) Filed: Jul. 28, 2015

(65) Prior Publication Data

US 2015/0327762 A1    Nov. 19, 2015

Related U.S. Application Data

(63) Continuation of application No. 13/247,307, filed on Sep. 28, 2011, now Pat. No. 9,125,593.

(30) Foreign Application Priority Data

Sep. 30, 2010   (JP) ................. 2010-223122

(51) Int. Cl.
*G06K 9/34* (2006.01)
*A61B 3/02* (2006.01)
(Continued)

(52) U.S. Cl.
CPC ............ *A61B 3/102* (2013.01); *A61B 3/0025* (2013.01); *A61B 3/0058* (2013.01);
(Continued)

(58) Field of Classification Search
CPC ......... A61B 5/00; A61B 3/0025; A61B 3/102; A61B 3/00; A61B 5/0066; A61B 3/14;
(Continued)

(56) References Cited

U.S. PATENT DOCUMENTS 5,315,329 A    5/1994   McAdams
7,510,282 B2   3/2009   Ueno et al.
(Continued)

FOREIGN PATENT DOCUMENTS

JP    H11-276437 A    10/1999
JP    2008-029467 A    2/2008
(Continued)

*Primary Examiner* — Sheela C Chawan
(74) *Attorney, Agent, or Firm* — Oliff PLC

(57) ABSTRACT

A method of observing a three-dimensional image of an examinee's eye to be examined, includes: obtaining a first three-dimensional image which is a three-dimensional image of an anterior segment of the examinee's eye by optical coherence tomography for obtaining a tomographic image by converging a measurement light on the anterior segment of the examinee's eye; obtaining a second three-dimensional image which is a three-dimensional image of a fundus of the examinee's eye by optical coherence tomography for obtaining a tomographic image by converging the measurement light on the fundus of the examinee's eye by a timing different from a timing of obtaining the first three-dimensional image; constructing a three-dimensional eyeball image of the examinee's eye through image processing based on the obtained first and second three-dimensional images; and displaying the constructed three-dimensional eyeball image on a monitor.

14 Claims, 7 Drawing Sheets

(51) Int. Cl.
*A61B 3/10* (2006.01)
*A61B 3/117* (2006.01)
*A61B 3/12* (2006.01)
*A61B 3/14* (2006.01)
*A61B 3/00* (2006.01)
*A61B 3/18* (2006.01)

(52) U.S. Cl.
CPC ............ *A61B 3/1005* (2013.01); *A61B 3/117* (2013.01); *A61B 3/12* (2013.01); *A61B 3/14* (2013.01); *A61B 3/18* (2013.01)

(58) Field of Classification Search
CPC ....... A61B 3/12; A61B 5/0073; A61B 5/0033; G06K 9/00; G06T 7/0075; G06T 2207/10012; G06T 11/003; G06T 2207/10101; G06T 2207/30
USPC ........ 382/173, 181, 255, 276, 154; 351/200, 351/205, 206, 211, 221, 208, 209, 246, 351/212, 210, 214, 222, 239, 237, 243; 600/410, 109
See application file for complete search history.

(56) References Cited

U.S. PATENT DOCUMENTS

| | | |
|---|---|---|
| 7,880,895 B2 | 2/2011 | Yamada et al. |
| 8,205,991 B2 | 6/2012 | Wei et al. |
| 8,672,480 B2 | 3/2014 | Isogai et al. |
| 9,125,593 B2 * | 9/2015 | Isogai ................ A61B 3/102 |
| 2008/0297724 A1 | 12/2008 | Shimizu et al. |
| 2010/0110172 A1 | 5/2010 | Satake |
| 2010/0231698 A1 | 9/2010 | Nakahata et al. |
| 2011/0267583 A1 | 11/2011 | Hayashi |

FOREIGN PATENT DOCUMENTS

| | | |
|---|---|---|
| JP | 2009-183332 A | 8/2009 |
| JP | 2010-110393 A | 5/2010 |

* cited by examiner

FIG.10A
FIG.10B
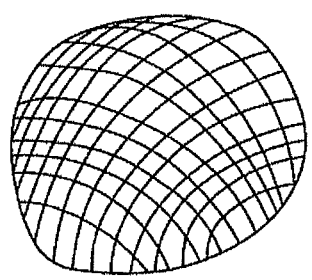
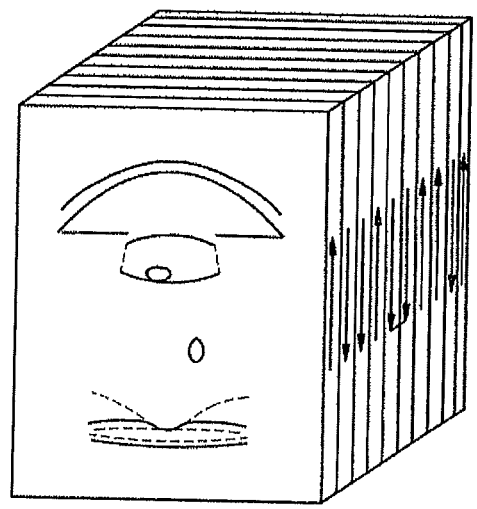

METHOD OF OBSERVING A THREE-DIMENSIONAL IMAGE OF EXAMINEE'S EYE

CROSS-REFERENCE TO RELATED APPLICATIONS

This application is a continuation application of U.S. patent application Ser. No. 13/247,307, filed on Sep. 28, 2011, which is based upon and claims the benefit of priority from the prior Japanese Patent Application No. 2010-223122 filed, on Sep. 30, 2010. The disclosures of the prior applications are hereby incorporated by reference herein in their entirety.

TECHNICAL FIELD

The present invention relates to a method of observing a three-dimensional image of an examinee's eye to be examined.

BACKGROUND ART

When an examinee's eye is observed and diagnosed, conventionally a tomographic image of an anterior segment is captured by an optical coherence tomography (OCT) dedicated to imaging the anterior segment, while a tomographic image of a fundus is captured by an OCT dedicated to imaging the fundus (see JP-A-2008-29467). A front image of the fundus is captured by a fundus camera or a scanning laser ophthalmoscope (SLO), and a front image of the anterior segment is captured by an ophthalmologic ultrasonic diagnostic apparatus or an anterior segment imaging apparatus (Scheimpflug).

DISCLOSURE OF THE INVENTION

Problems to be Solved by the Invention

However, the conventional method can only create images from different imaging data separately from one another, and discretely analyze and display each of the obtained images, thereby making it difficult to observe the general condition of an eye at once.

The present invention provides a method which enables a macroscopic observation of an examinee's eye to be examined.

Means of Solving the Problems

To achieve the above purpose, one aspect of the invention provides a method of observing a three-dimensional image of an examinee's eye to be examined, including: obtaining a first three-dimensional image which is a three-dimensional image of an anterior segment of the examinee's eye by optical coherence tomography for obtaining a tomographic image by converging a measurement light on the anterior segment of the examinee's eye; obtaining a second three-dimensional image which is a three-dimensional image of a fundus of the examinee's eye by optical coherence tomography for obtaining a tomographic image by converging the measurement light on the fundus of the examinee's eye by a timing different from a timing of obtaining the first three-dimensional image; constructing a three-dimensional eyeball image of the examinee's eye through image processing based on the obtained first and second three-dimensional images; and displaying the constructed three-dimensional eyeball image on a monitor.

BRIEF DESCRIPTION OF THE DRAWINGS

FIGS. 10A and 10B are diagrams showing an example of correcting positional shift (deviation) of an OCT tomographic image by use of corneal topography measuring results.

DESCRIPTION OF THE EMBODIMENTS

Figure 1:
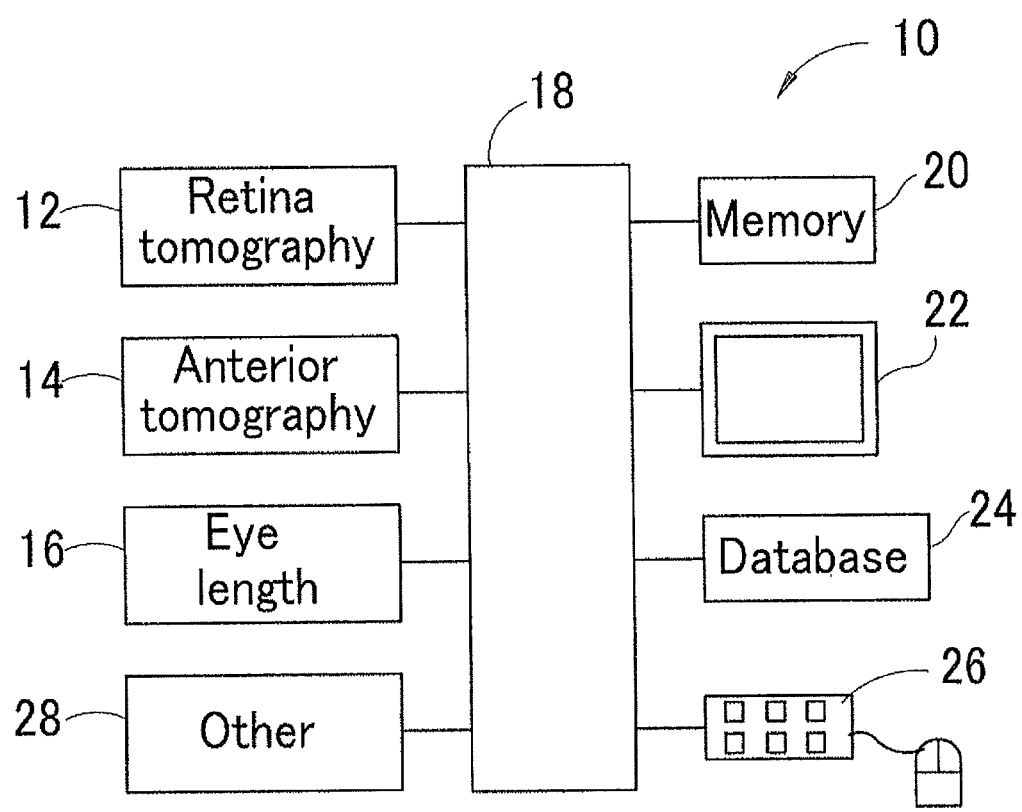
FIG. 1 is a diagram showing an optical system and a control system of an ophthalmologic observation system according to a present embodiment.

An embodiment of the present invention is described with reference to the accompanied drawings. FIG. 1 is a block diagram illustrating an optical system and a control system of an ophthalmologic observation system according to the present embodiment. In the description of the embodiment given below, the axial direction of an examinee's eye (eye E) is called Z direction (direction of optical axis L1), the horizontal direction thereof is called X direction, and the vertical direction thereof is called Y direction.

<System Configuration>

An ophthalmologic observation system 10 includes a fundus tomography imaging device 12, an anterior segment tomography imaging device 14, and an eye distance measuring device 16. These devices are connected to a processor (arithmetic control unit) 18. The processor 18 is connected to a memory 20, a monitor 22, a database (for example, normal eye condition DB) 24, and an operation unit 26. Various interface devices (for example, mouse, touch panel) can be used as the operation unit 26.

The fundus tomography imaging device 12 obtains a three-dimensional tomographic image of a fundus Ef. The anterior segment tomography imaging device 14 obtains a three-dimensional tomographic image of an anterior segment Ea. The image data thus obtained is transferred to and stored in the memory 20. The devices 12 and 14 may be housed in a cabinet or may be located apart from each other as independent devices. These devices may be configured to simultaneously capture the images of the fundus and the anterior segment.

An ophthalmologic optical interference tomography (OCT optical system 200 (see FIG. 2)) is used. In addition to these devices, an intermediate segment tomography imaging device configured to capture a three-dimensional tomographic image of an intermediate light-transmittable segment situated between the fundus and the anterior segment (for example, posterior surface of crystalline lens-vitreous-retina) is provided in the cabinet where the devices 12 and 14 are housed or provided apart from these devices as an independent device.

The eye distance measuring device 16 irradiates light or ultrasonic wave on the eye E to obtain a reflected signal therefrom, and thereby measures inter-tissue lengths of the eye E in the axial direction (for example, ocular axial length, distance from anterior surface of crystalline lens to retinal surface). For example, the device 16 is provided in the cabinet where the fundus tomography imaging device 12 and the anterior segment tomography imaging device 14 are housed. The device 16 may be provided apart from these devices as an independent device so that a measurement result thereby obtained can be used.

The processor 18 is connected to a device 28 configured to capture tomographic images of the eye E in a manner different from the optical coherence tomography. For example, an ultrasonic diagnostic apparatus is suitably used for capturing a tomographic image of the back side of iris (conventionally difficult to obtain the tomographic image by the OCT because a measurement light fails to reach the back side of iris). A fundus camera designed to obtain a color image of the fundus and an SLO designed to scan the fundus are suitable devices for capturing a front image of the fundus. A corneal topography measuring apparatus is suitably used to measure the distribution of a three-dimensional corneal shape in a shorter amount of time than the OCT.

<Constructing and Displaying Eyeball Graphic>

The processor 18 calculates a three-dimensional positional information of the whole eye including the fundus and the anterior segment (may also include the intermediate segment) based on the image data and measured data obtained by the devices 12, 14, and 16, and constructs a three-dimensional graphic 300 representing a three-dimensional shape of the whole eye (hereinafter, simply called eyeball image) through image processing (see FIG. 3). Thus, the tomographic images of the fundus and the anterior segment are three-dimensionally synthesized to create a three-dimensional tomographic image data of the whole eye. To create the three-dimensional tomographic image data, the computer graphic technique (CG) is employed. To construct the three-dimensional graphic, it is unnecessary to obtain all of the image data (for example, peripheral portion of the eyeball) and optical data of the whole eye E. A virtual graphic created based on the known eye structure may be used to interpolate the data.

The processor 18 controls the display of the monitor 22 and outputs an eyeball image 300 which is a three-dimensional image of the whole eye. When the processor 18 displays the eyeball image 300, the eyeball image 300 is cut in a cross section thereof so that tomographic images of tissues of the anterior segment and tissues of the fundus are visible. When thus displayed, the internal tissues of the anterior segment and the fundus can be visually confirmed. The eyeball image 300 illustrated in FIG. 3 includes the three-dimensional representation of a graphic image 302 of the fundus, a graphic image 304 of the anterior segment, and a graphic image 306 of the intermediate segment.

The processor 18 changes a display position, a display direction, and a display magnifying power of the eyeball image 300 based on an operation signal outputted from the operation unit 26 manipulated by an examiner. Accordingly, the eyeball image 300 is arbitrarily rotated so that a direction where the eyeball image 300 is viewed (for example, retina; front direction, oblique direction) can be arbitrarily adjusted.

Figure 4:
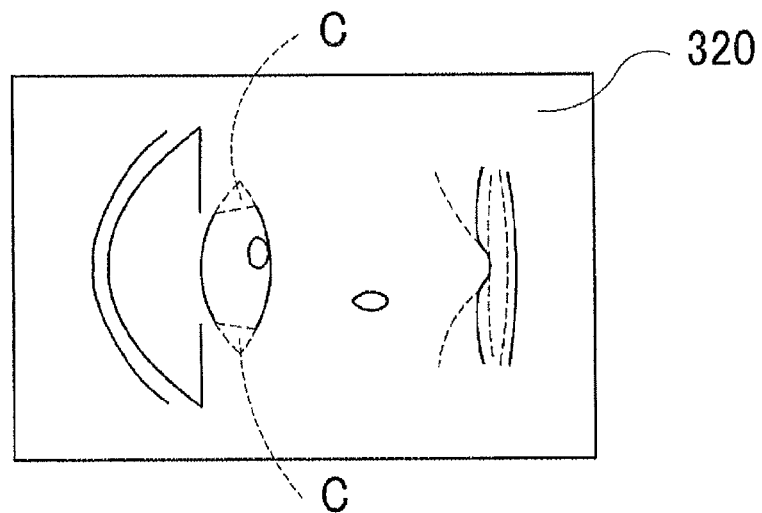
FIG. 4 is a diagram showing a display example of a tomographic image in a traverse direction of the entire eye.

The processor 18 may be configured to display a tomographic image 320 in a traverse direction of the whole eye based on the three-dimensional positional information of the whole eye (see FIG. 4). The eyeball image 300 and the tomographic image 320 both may be displayed at the same time. At a tomographic position on the eyeball image 300 corresponding to the tomographic image 320, a graphic display 310 indicating the tomographic position may be, for example, synthetically displayed so as to overlap on the eyeball image 300. The processor 18 changes the traverse direction of the tomographic image 320 obtained from the three-dimensional positional information based on the operation signal outputted from the operation unit 26.

Figure 5A:
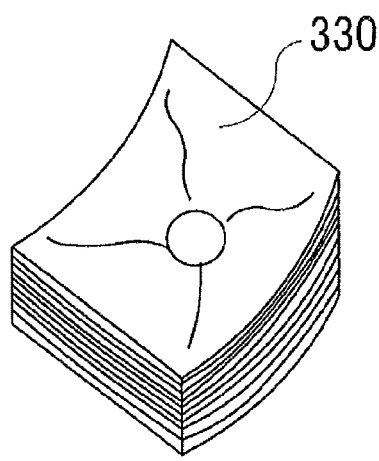
FIG. 5A is a diagram showing a display example of a three-dimensional image of a fundus.
Figure 5B:
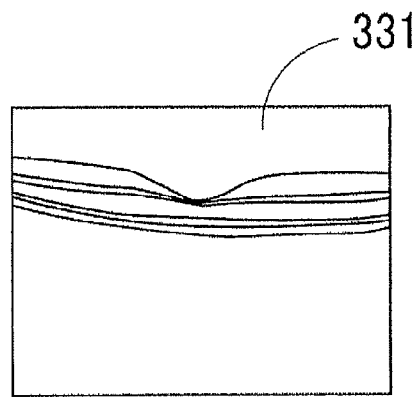
FIG. 5B is a diagram showing a display example of a cut-out image of the fundus.

When any arbitrary region of the eyeball image 300 is selected by the operation unit 26, the arbitrary region is cut out to be displayed, or a degree of transmissivity thereof is changed. When the examiner wants to observe any particular site (for example, tomographic image of fundus), an image of the particular site is displayed in a display mode suitably set for each site (see a three-dimensional image 330 of the fundus illustrated in FIG. 5A, a cut-out image 331 of the fundus illustrated in FIG. 5B).

When, for example, a particular site of the eyeball image 300 is selected on the monitor 22, a tomographic image (2D image or 3D image) corresponding to the selected site is displayed on the monitor 22. Alongside of the displayed tomographic image, a measurement result (measurement map, etc.) and an analysis result of the selected site are displayed. When, for example, the fundus of the eyeball image 300 is selected, the tomographic image of the fundus is displayed with the eyeball image 300 on the monitor 22. The other information displayed then with the tomographic image of the fundus are, for example, a thickness map in a retinal layer, a differential map relating to thicknesses of an eye in normal condition and the examined eye, and parameters indicating any pathological progress.

When an image corresponding to the particular site is being displayed on the monitor 22, a part of the eyeball image 300 corresponding to the particular site is highlighted (for example, displayed in a different color, displayed with a mark appended thereto) so that the eyeball image 300 and the tomographic image of the particular site can be referenced to each other.

When, for example, a three-dimensional tomographic image of the particular site is displayed, a part of the eyeball image 300 corresponding thereto is highlighted. When, for example, a two-dimensional tomographic image of the particular site in a traverse direction thereof is displayed, a part of the eyeball image 300 is displayed such that a traverse position is indicated. The eyeball image 300 reduced in size with a part of the eyeball image 300 corresponding to the particular site being highlighted may be displayed alongside of the image of the particular site.

<Image Addition Using Another Device>

When any image is added by a difference device, the processor 18 may fetch non-OCT information based on the image data or measured data obtained by the device 28 and synthesize the fetched information with the eyeball image 300 or the tomographic image 320 to display a synthesized image, or any of the image data obtained by the devices 12, 14, and 16 may be synthesized with the data obtained by the device 28.

Figure 3:
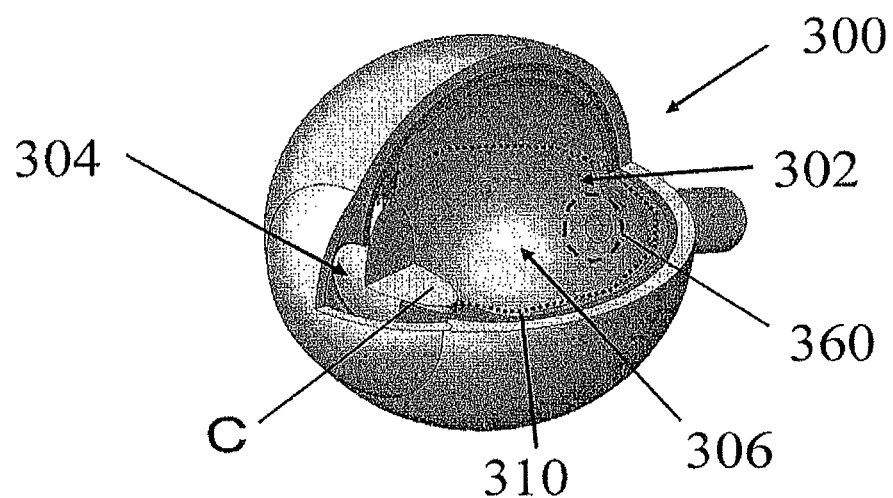
FIG. 3 is a diagram showing a display example of an eyeball three-dimensional image.

When an ultrasonic echo image obtained by a ultrasonic diagnostic apparatus is synthetically displayed in a back-side region of iris in the eyeball image 300, image information of the back-side region of iris (for example, shape of the peripheral portion of crystalline lens) is added (for example, see image C illustrated in FIGS. 3 and 4). In the ultrasonic echo image and a region where the OCT image overlap with each other, one of the images with a higher image quality is preferentially displayed (usually, OCT image). To obtain an image of the anterior segment using light is suitable for obtaining images of any light-transmittable regions (in pupil), however, it is difficult to obtain any image of the back side of iris using light. Therefore, the eyeball image 300 synthesized with the ultrasonic image is more usefully informative. Alternatively, a graphic map based on a corneal topography measurement result may be synthesized with a part of the eyeball image 300 corresponding to the cornea.

<Image Analysis, and Reflection of Analysis Result on Eyeball Graphic>

The processor 18 combines the image information of the anterior segment, intermediate segment, and fundus and analyzes detailed shape, condition, disorder, and abnormality of the whole eye through image processing, and displays an analysis result thereby obtained on the monitor 22. For example, the processor 18 analyzes the captured images and displays an analysis result thereby obtained with a three-dimensional graphic (for example, see a part marked with 360). When, for example, any disorder or abnormality is detected by the analysis, the processor 18 displays a part of the eyeball image 300 corresponding to the abnormal site as a point of attention (for example, displayed with an additional mark appended thereto, highlighted, displayed in a different color, or displayed in a blinking manner). The processor 18 may separately analyze the respective image data obtained by the devices or analyze the synthesized image data obtained by synthesizing the respective data.

The analysis results of the different sites relate to, for example; corneal shape, corneal thickness, anterior chamber depth, crystalline lens shape, retinal thickness, ocular axial length, and result of comparison to the normal eye condition database (may be displayed in the form of numeral values or color map).

When the tomographic image of the fundus is analyzed, the processor 18, for example, detects retinal layers in the obtained three-dimensional tomographic image through image processing, and analyzes detection results of the respective layers based on a given judgment condition (judgment criterion) to determine whether the imaged site is in normal condition or not. This determination can be made by, for example, judging thicknesses of the respective layers, shape irregularity, or dimension of the imaged site. The basic data that can be used as the image judgment condition is a database in which inter-layer intervals and shape and dimension of the particular site in normal eye condition, for example, are stored. Then, it is judged whether or not the thicknesses of a nerve fiber layer of the eye E stays within the data range of normal eye condition.

To analyze the tomographic image of the anterior segment, the processor 18, for example, calculates positional information/luminance information of the anterior segment tissues in the obtained three-dimensional tomographic image. Then, the processor 18 measures based on the calculated positional information; retinal surface/back surface curvature distribution, corneal thickness distribution, front surface/back surface curvature distribution of crystalline lens, crystalline lens thickness distribution, anterior chamber thickness depth, and a tilting degree of gonioangle (opening degree). For example, it is judged whether or not the tilting degree of gonioangle in the eye E is beyond an allowed range. Further, a degree of opacity of the crystalline lens is calculated based on the luminance distribution of the crystalline lens image to analyze a stage of cataract progression.

To analyze the tomographic image of the intermediate segment, the processor 18, for example, calculates the luminance information of tissues of the intermediate segment in the obtained three-dimensional tomographic image. Then, a degree of transmissivity of vitreous is calculated based on the luminance distribution of the vitreous image to analyze, for example, exfoliation of the vitreous and any hemorrhage to the vitreous.

<Integrated Analysis>

Further, the processor 18 integrally analyzes the analysis results of the respective tomographic images. The processor 18, for example, may judge a stage of glaucoma based on the tilting degree of gonioangle in the image of the anterior segment and the thickness of a retinal layer (for example, nerve fiver layer) in the image of the fundus. In the event that the gonioangle degree stays within an allowed range but the retinal layer thickness is beyond an allowed range, an examinee is suspected to have low-tension glaucoma. This judgment result is displayed on the monitor 22.

The processor 18 may be configured to measure eyeball tissues based on the obtained three-dimensional positional information of the whole eye. For example, the processor 18 extracts a corneal apex position and a macular (yellow spot) position of the fundus from the three-dimensional positional information through image processing and calculates a distance from the corneal apex position to the yellow spot position to measure the ocular axial length. This succeeds in accurately calculating the ocular axial length of the eye E regardless of the tilting degree of the eyeball. To more accurately calculate the ocular axial length, the images of the anterior segment and the fundus are both obtained at the same time.

The processor 18 analyzes the eye E based on the image information/measurement information obtained by the device 28 and displays an analysis result thereby obtained on the monitor 22. In the case where lesion, edema, or opacity is detected on the back side of iris in the analysis by the ultrasonic diagnostic apparatus, for example, the processor 18 displays a part of the eyeball image 300 corresponding to the back side of iris as a point of attention. In the case where conical cornea is detected when the corneal topography is analyzed, the processor 18 displays a part of the eyeball image 300 corresponding to the cornea as a point of attention.

The processor 18 analyzes the eye E based on the image information obtained by the devices 12 and 14 and the image information obtained by the device 28 and displays an analysis result thereby obtained. For example, the processor 18 judges a degree of opacity in the whole crystalline lens based on a center image of the crystalline lens obtained by the anterior segment OCT and a peripheral image of the crystalline lens obtained by the ultrasonic diagnostic apparatus and display a degree of cataract progression as a judgment result (for example, graphic display, parameter display).

Such an integrated analysis based on the analysis result by the OCT and the analysis result by the non-OCT apparatus leads to a more detailed and precise analysis. The integrated analysis uses, for example, fundus camera images, ultrasonic images, and refraction mapping data. The integrated analysis may use the OCT analysis result and an analysis result obtained by X-ray radiography, MRI, terahertz wave radar, and millimeter wave radar.

The processor 18 may be arranged to display information which assists a surgical operation of the eye E. For example, the processor 18 obtains optical information of the eye E (for example, corneal curvature, ocular refractive power, ocular axial length, aberration information) and optical information of an intraocular lens, and performs a simulation of an intraocular lens operation based on the pieces of obtained optical information. To perform the simulation, any necessary information for calculation of the intraocular lens such as refraction-related data is obtained by another apparatus (for example, corneal topography, ocular refractive power measuring apparatus), and the pieces of information are integrally analyzed (or an integrated apparatus may be used).

Figure 6:
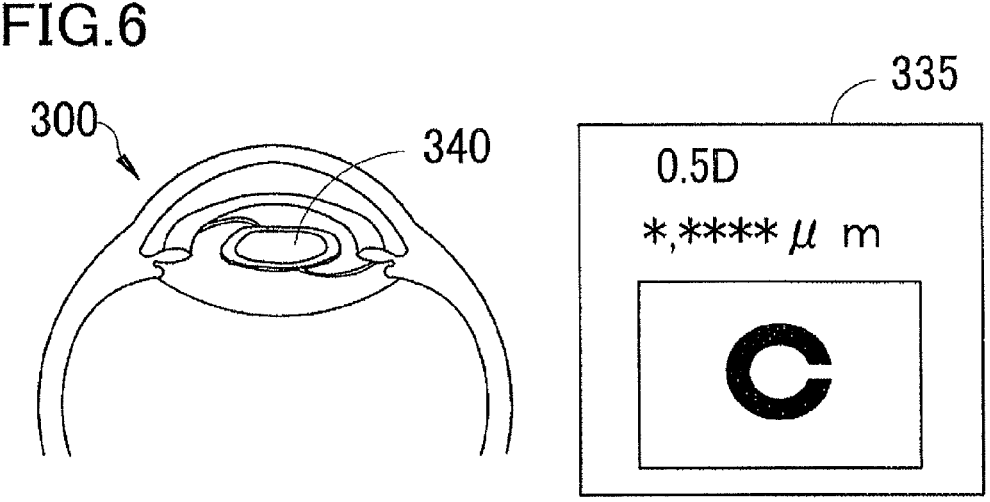
FIG. 6 is a diagram showing an example of a case where a simulation of an intraocular lens operation using an eyeball image.

The processor 18 synthetically displays a lens graphic 340 representing the intraocular lens in the anterior segment of the eyeball image 300, and also displays a prospective postoperative outcome 335 depending on the location of the lens (for example, residual refractivity, residual aberration, visibility simulation) (see FIG. 6). Whenever the lens graphic 340 is positionally changed on the eyeball image 300 by manipulating the operation unit 26, the prospective postoperative outcome 335 by the intraocular lens is accordingly updated. Thus, the intraocular lens can be simulated.

To obtain the tomographic images of the anterior segment, fundus, intermediate segment, and the whole eye, any of the ultrasonic diagnostic apparatus, anterior segment tomography imaging apparatus which uses slit light (for example, slit projection system and Scheimpflug camera), X-ray radiographic apparatus, imaging apparatus using magnetic resonance imaging (MRI), and imaging apparatus using terahertz wave radar or millimeter wave radar may be used. These apparatuses may be combined with the OCT to constitute a multiple function apparatus. As the devices 12 and 14 may be used devices which employ different imaging techniques.

<Constructing Eyeball Image Using OCT Optical System>

Figure 2:
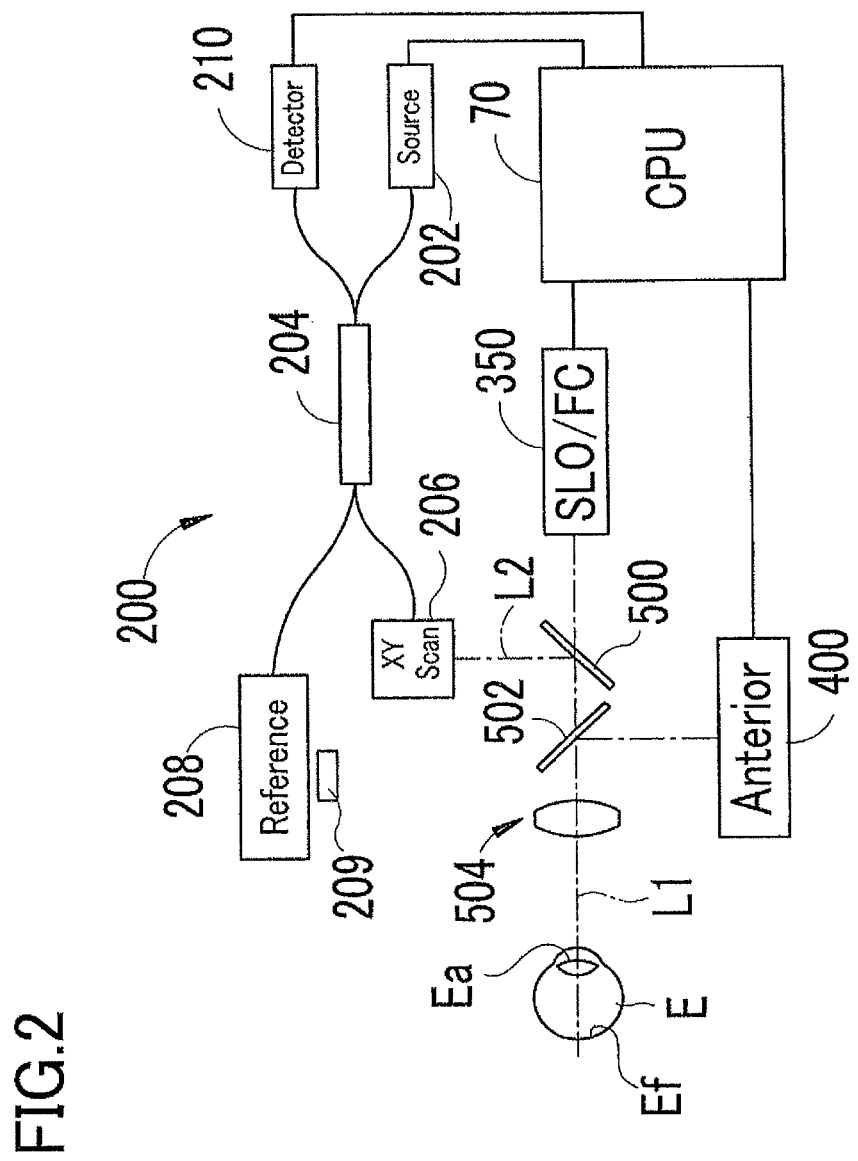
FIG. 2 is a diagram showing one example of an ophthalmologic imaging apparatus including an OCT optical system according to the present embodiment.

FIG. 2 is an illustration of an ophthalmologic imaging apparatus provided with the OCT optical system 200. In the description given below, the depth direction of the eye E is called Z direction, the horizontal direction thereof is called X direction, and the vertical direction thereof is called Y direction.

This optical system has the OCT optical system (optical interference system) 200 for obtaining the tomographic images of the eye E, a front imaging optical system 350 for obtaining a front image of the fundus Ef, and an anterior segment imaging optical system 400 for obtaining a front image of the anterior segment Ea. These optical systems are housed in a cabinet and three-dimensionally moved toward and away from the eye E by a conventional transport mechanism for alignment (manual or electrically driven).

A dichroic mirror 500 is characterized in reflecting a measurement light emitted from a light source 202 of the OCT optical system 200 and letting a light emitted from a light source of the front imaging optical system 350 pass therethrough. A dichroic mirror 502 reflects a light irradiated on the anterior segment by an anterior lighting unit not illustrated in the drawings and lets a resulting reflected light enter through the anterior segment imaging optical system 400. A light-guiding optical system (for example, object lens) 504 guides the respective lights to the eye E and guides the lights reflected from the eye E to the respective optical systems.

The OCT optical system 200 splits a light flux emitted from the light source 202 into a measurement light flux and a reference light flux using a coupler 204. The OCT optical system 200 guides the measurement light flux to a predefined site of the eye E (anterior segment Ea or fundus Ef) and guides the reference luminance flux to a reference optical system 208. Then, the OCT optical system 200 makes a detector (photo detector) 210 receive an interfering light obtained by synthesizing the measurement light flux reflected from the predefined site of the eye E with the reference light flux.

The optical system is a SS-OCT (swept source OCT) optical system. As the light source 202 is used a wavelength scanning light source (wavelength-variable light source) in which an outgoing wavelength changes with time. For example, a light source, a fiver ring resonator, or a wavelength-selectable filter constitutes the light source 202. Examples of the wavelength-selectable filter are combination of a polygonal mirror and diffraction grating, and a Fabry-Perot etalon filter. The detector 210 is provided with a photo detector or provided with a plurality of photo detectors for balanced detection and polarized detection.

As to the outgoing wavelength of the light source 202, a light source which generates a light having a center wavelength in the range of $\lambda=800$ to 1100 nm is used to capture the tomographic image of the fundus, and a light source which generates a light having a center wavelength in the range of $\lambda=1200$ to 1600 nm is used to capture the tomographic image of the anterior segment (particularly when the gonioangle is imaged). When only one light source is used to image both the fundus and the anterior segment, the light source which generates a light having a center wavelength in the range of $\lambda=800$ to 1100 nm is used. When an integrated apparatus where the fundus OCT and the anterior segment OCT are combined is used, the light source 202 may be provided with a first light source for fundus and a second light source for anterior segment so that one of the first and second light sources is selectively used depending on a site to be imaged.

By changing at least one of a wavelength width (wavelength band) of the light emitted from the light source 202 and the number of sampling points in the wavelength width, a target imaging range in the depth direction and a degree of resolution are changed. To broaden the target imaging range, for example, a light source having a large wavelength width (broadband light source) is used to reduce a sampling time of the wavelength width so that the number of sampling points is increased.

To obtain the tomographic image of the whole eye covering the cornea through the fundus (large-depth imaging), a wavelength-variable light source having a relatively large wavelength width (for example, variation by approximately 100 nm) is used so that the target imaging range in the depth direction is set in the whole eye so as to cover the cornea through the fundus.

To obtain the tomographic images of the respective sites (anterior segment, intermediate segment, fundus) with a high resolution (high-resolution imaging), a wavelength-variable light source having a relatively short wavelength width (for example, 50 nm) is used so that the target imaging range in the depth direction is set for each of the sites (anterior segment, intermediate segment, fundus) to obtain high-resolution tomographic images of the respective sites. The target imaging range when the light source is used is set narrower than that of the large-depth imaging and included in at least a part of a site to be imaged.

In the case of such an apparatus that is capable of both the large-depth imaging and the high-resolution imaging, the light source 202 may be provided with a first light source for large-depth imaging and a second light source for high-resolution imaging so that one of the first and second light sources is selectively used depending on an intended imaging purpose. In that case, a sampling time of a light receiving signal may be changed, or at least one of the wavelength width and the sampling time may be changed depending on the imaging purpose.

The optical path of the measurement light is provided with an optical scanner (light scanning unit) 206 which changes (deflects) a traveling direction of the measurement light flux to enable scanning in X-Y directions using the measurement light. Examples of the optical scanner 206 are a reflector mirror which changes a light reflection direction (galvano mirror, polygonal mirror, resonant scanner), an acousto-optic modulator (AOM) which changes a light traveling direction, and a micro-mirror device.

The light-guiding optical system 504 is described. To obtain the tomographic image of the fundus, the optical system is set so that the measurement light flux converges on the fundus. To obtain the tomographic image of the anterior segment, the optical system is set so that the measurement light flux converges on the anterior segment. To change a focal point between the fundus and the anterior segment, for example, an attachment lens is attached to a test window, or a lens is inserted in and removed from an optical path. To obtain the images of the anterior segment and the fundus at the same time, the optical system is set so that the measurement light flux converges on the fundus.

The reference optical system 208 may be a reflection reference optical system illustrated in FIG. 2 or a light-transmittable reference optical system. An optical path difference adjuster 209 is provided in the optical path of the measurement light or the reference light so as to change an optical path difference between optical path lengths of the measurement light and the reference light. For example, a reflector mirror provided in the reference optical system 208 is moved by a motor in the direction of optical axis, and fibers provided in the optical path of the measurement light is moved in the direction of optical path relative to the optical scanner 206. Thus, the optical path lengths to a site to be imaged can be adjusted.

To obtain the tomographic image of the fundus, the optical path difference adjuster 209 adjusts the optical path difference so that the optical path length of the measurement light irradiated on the fundus and the optical path length of the reference light are equal to each other. To obtain the tomographic image of the anterior segment, the optical path difference adjuster 206 adjusts the optical path difference so that the optical path length of the measurement light irradiated on the anterior segment and the optical path length of the reference light are equal to each other. To obtain the images of the whole eye at once, the optical path difference adjuster 206 adjusts the optical path difference so that the tomographic images of the whole eye can be obtained.

Figure 7A:
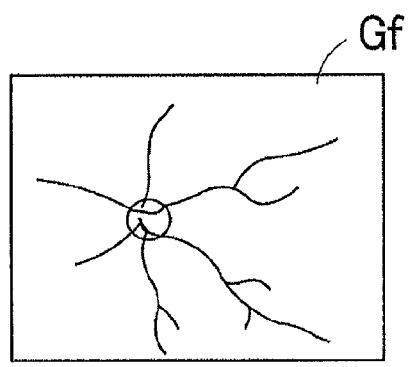
FIG. 7A is a diagram showing a display example of a front image.
Figure 7B:
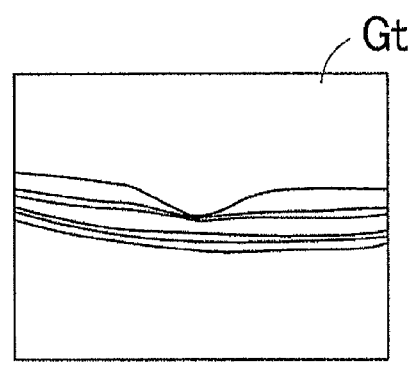
FIG. 7B is a diagram showing a display example of a tomographic image.

A control unit 70 controls driving of the optical scanner 206 to form the tomographic images through image processing based on the light receiving signal outputted from the detector 210. The obtained tomographic images are outputted to the monitor 22 as still images or moving images (see front image Gf illustrated in FIG. 7A, tomographic image Gt illustrated in FIG. 7B), and also stored in the memory 20.

The light emitted from the light source 202 passes through the coupler 204, the optical scanner 206, the dichroic mirror 500, the dichroic mirror 502, and the light-guiding optical system 504 to be finally irradiated on the eye E. The reflected light from the fundus generated by the reference light and the measurement light is synthesized by the coupler 204 into an interfering light, and then detected by the detector 210.

When the wavelength of the light emitted from the light source 202 changes with time, the wavelength of the interfering light received by the detector 210 changes. When the spectrum data of the interfering light detected by the detector 210 is inputted to the control unit 70 and the frequency of the interfering light is analyzed by means of Fourier transform, information in the depth direction of the eye E (A scan signal) can be measured. As the outgoing wavelength of the light source 202 repeatedly changes at given intervals, the A scan signal is periodically obtained.

The control unit 70 makes the optical scanner 206 run the measurement light on the eye E in a given traverse direction to obtain the tomographic images. When the control unit 70 two-dimensionally runs the measurement light to scan in X-Y directions, the three-dimensional tomographic images of the eye E can be obtained. The obtained tomographic images are displayed on the monitor 22 as moving images or still images.

Examples of the front imaging optical system 350 are scanning laser ophthalmoscope (SLO) and fundus camera. The SLO makes an optical scanner run a light emitted from a light source on the fundus to scan and then makes a photo detector receive a reflected light from the fundus through a confocal aperture provided at such a position that is substantially conjugate with the fundus. The fundus camera irradiates light on the whole fundus at once and captures a reflected image thereby obtained using a two-dimensional imaging device. An imaging light source is a visible light source or an infrared light source. As a result, the front image of the fundus is obtained. A moving image is used to observe the fundus, and a still image is stored with the tomographic image.

Figure 8:
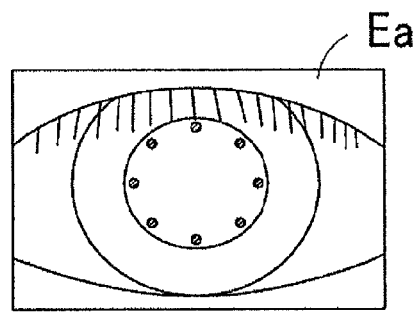
FIG. 8 is a diagram showing a display example of an image of the anterior segment.

The imaging optical system 400 has an imaging device (for example, two-dimensional imaging device) which captures a reflected image of the anterior segment resulting from light irradiation by the infrared light source through the light-guiding optical system. An output from the imaging device is transmitted to the control unit 70, and the image of the anterior segment Ea captured by the imaging device is displayed on the monitor 22 (see FIG. 8). A still image of the anterior segment is stored in the memory 20 with the tomographic image.

An operation of the ophthalmologic imaging apparatus thus structurally characterized is described below. An apparatus used in the description given below is an integrated apparatus capable of imaging the anterior segment and the fundus both and also capable of the large-depth imaging. Some different imaging modes are provided in the apparatus, which are; anterior segment imaging mode for obtaining the three-dimensional tomographic image of the anterior segment, fundus imaging mode for obtaining the three-dimensional tomographic image of the fundus, and a large-depth imaging mode for imaging the region from the anterior segment through the fundus. One of the modes is selected and set by way of the operation unit 26.

<Fundus Imaging Mode>

First, the fundus imaging mode is described. The optical system is preconfigured to support the imaging of the fundus. An examiner requests an examinee to be examined to gaze a fixation lamp not illustrated in the drawings and then performs an alignment relative to the fundus. The control unit 70 drives the adjuster 209 based on the light receiving signal outputted from the detector 210 to adjust the optical path difference between the measurement light and the reference light so that the tomographic image of the fundus is obtained.

In response to a given trigger signal thereafter outputted, the control unit 70 drives the optical scanner 206 so as to raster-scan a rectangular region on the fundus Ef using the measurement light to obtain depth profiles at X-Y positions. As a result, three-dimensional OCT data of the fundus Ef with a high resolution is obtained and stored in the memory 20.

<Anterior Segment Imaging Mode>

Next, the anterior segment imaging mode is described. The optical system is preconfigured to support the imaging of the anterior segment. The examiner performs an alignment relative to the anterior segment. When a given trigger signal is outputted, the control unit 70 drives the optical scanner 206 so as to raster-scan a rectangular region on the anterior segment Ea using the measurement light so that depth profiles are obtained at X-Y positions. As a result, three-dimensional OCT data of the anterior segment Ea with a high resolution is obtained and stored in the memory 20.

<Large-depth Imaging Mode>

Next, the large-depth imaging mode is described. The optical system is preconfigured to support the large-depth imaging. The examiner performs an alignment relative to the eye E. When a given trigger signal is outputted, the control unit 70 drives the optical scanner 206 so as to raster-scan a rectangular region on the whole eye Ea using the measurement light so that depth profiles are obtained at X-Y positions. As a result, three-dimensional OCT data of the whole eye E is obtained as a template image and then stored in the memory 20.

<Detailed Imaging Mode>

If necessary, the respective sites are OCT-imaged in a more detailed manner in the respective imaging modes described so far. The control unit 70 obtains the tomographic images based on preset scan positions/patterns and stores the obtained images in the memory 20. The control unit 70 obtains a plurality of tomographic images at one scan position and adds the images to obtain an average image so that a tomographic image with a better image quality is obtained and used for a microscopic analysis. Examples of scan pattern are line scan, cross scan, circle scan, and radial scan; cross scan or radial scan for the cornea, scan for the gonioangle, cross scan, radial scan, or multi scan for the fundus, and circle scan for papilla.

In the imaging modes, the control unit 70 obtains the front image of the fundus captured by the imaging optical system 300 and the image of the anterior segment captured by the imaging optical system 400 at substantially the same time as obtaining the three-dimensional OCT data and stores the obtained images in the memory 20.

<Integrating Tomographic Image Data>

Figure 9:
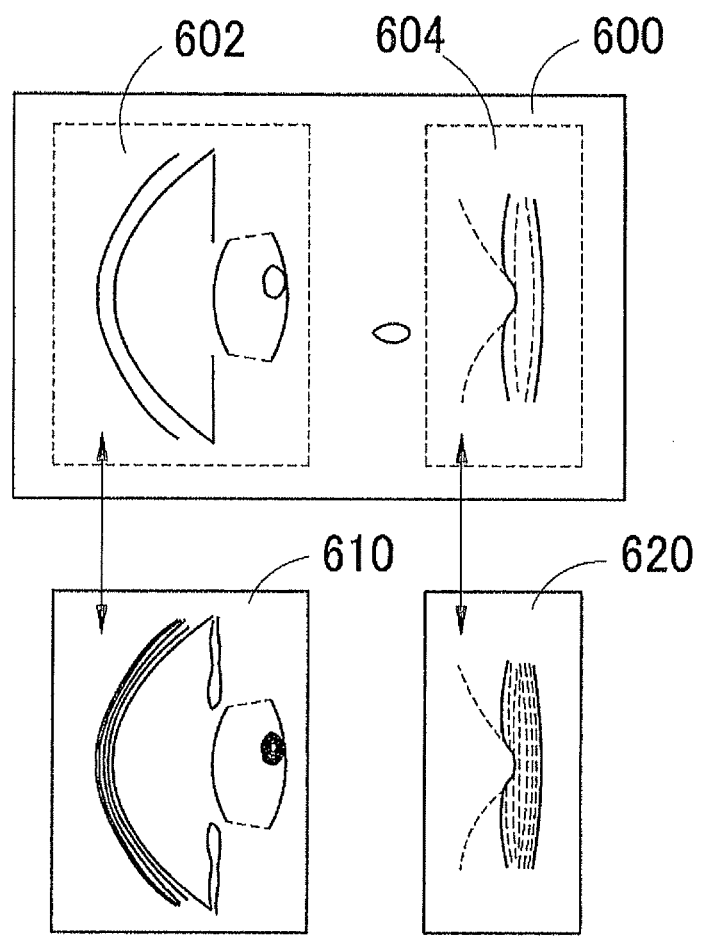
FIG. 9 is a diagram showing one example of respectively associating anterior segment data and fundus data with eyeball data obtained by large-depth imaging.

When the image data of the tomographic images are thus obtained, the control unit 70 associates an anterior segment data 610 and a fundus data 620 with an eyeball data 600 obtained by the large-depth imaging (see FIG. 9). Further, the tomographic data obtained in the detailed imaging mode is associated with the eyeball data directly or by way of the tomographic data of the respective sites (anterior segment data, fundus data).

For example, the control unit 70 obtains a three-dimensional correlativity between an image information 602 of the anterior segment in the eyeball data and an image information 610 of the anterior segment data to perform a matching process with a high correlativity. The three-dimensional shape of the anterior segment (for example, shapes of cornea, iris, and crystalline lens) and characteristic patterns in the anterior segment (for example, iris pattern), for example, are used as reference data of the matching process.

Similarly, the control unit 70 obtains a three-dimensional correlativity between an image information 604 of the fundus in the eyeball data and an image information 620 of the fundus data to perform a matching process with a high correlativity. The three-dimensional shape of the fundus (for example, surface shape of fundus, and shapes of retinal layers), and characteristic patterns in the fundus (for example, running pattern of blood vessels in the fundus), for example, are used as reference data of the matching process.

Accordingly, coordinate positions of the eyeball data and the anterior segment data (or fundus data) are associated with each other. Therefore, when a position on the anterior segment data or the fundus data is selected, a position on the eyeball data corresponding thereto is identified.

When the anterior segment data and the fundus data are associated with each other based on the eyeball data obtained by the large-depth imaging as basic data, a positional relationship between the high-resolution image of the anterior segment and the high-resolution image of the fundus is determined. As a result, favorable eyeball data can be obtained even if the apparatus and the eye E are positionally shifted to each other when the anterior segment and the fundus are imaged.

<Correction of Positional Shift of Eyeball Image Using Corneal Topography>

The three-dimensional tomographic images adjacent to each other may positionally shift to each other in the X-Y-Z directions due to any movement of the eye E when the image is obtained. To deal with such a positional shift, a measurement result obtained by a corneal topography measuring apparatus capable of measuring a three-dimensional topography of the corneal surface in a short time may be used to correct any positional shift between the three-dimensional tomographic images through image processing.

The corneal topography measuring apparatus includes, for example, a projection optical system provided with a measurement indicator for measuring a corneal surface shape distribution of the eye E (for example, multiple ring indicator, lattice pattern indicator) to project the measurement indicator toward the surface of a cornea Ec surface, and an imaging optical system which images the measurement indicator projected on the cornea Ec in a front direction using an imaging device (for example, anterior segment front imaging optical system), wherein the three-dimensional shape of the corneal surface is measured based on an imaging result of the measurement indicator obtained by the imaging device (for example, see JP-A-11(1999)-276437).

The control unit 70 performs a matching process between the three-dimensional topographic data and the three-dimensional tomographic data so that the three-dimensional shape of the corneal surface in the three-dimensional tomographic image of the eye (see FIG. 10B) is equal to the three-dimensional shape of the corneal surface (see FIG. 10A) obtained by the corneal topography measuring apparatus (see FIGS. 10A and 10B).

By moving and rotating the eyeball data relative to the topographic data through image processing, the control unit 70 performs a matching process so that a three-dimensional correlativity is increased between the three-dimensional shape of the corneal surface in the topographic data and the three-dimensional shape of the corneal surface in the eyeball data.

Then, the control unit 70 adjusts a positional relationship between a corneal apex in the topographic data and a corneal apex in the eyeball data. Next, the control unit 70 moves the tomographic images of the eye in traverse directions constituting the three-dimensional eyeball data (B scan images including the anterior segment and the fundus) in the Z direction through image processing so as to follow the three-dimensional shape of the topographic data.

Accordingly, any positional shift between the tomographic images constituting the eyeball data is corrected so that the three-dimensional eyeball data can be accurately obtained. Such a positional shift correction is similarly applicable to any positional shift between the topographic data and the three-dimensional data of the anterior segment data.

<Positional Shift Correction of Tomographic Data in Respective Sites Using Positionally-corrected Eyeball Data>

The positionally-corrected three-dimensional eyeball data is used to correct any positional shift in at least one of the three-dimensional data of the anterior segment and the three-dimensional data of the fundus. For example, the control unit 70 performs a matching process between the eyeball data and the fundus data so that the three-dimensional shape of the fundus tomographic image is equal to the three-dimensional shape of the positionally-corrected tomographic image of the eye. A description is given below referring to the positional shift correction in the fundus.

By moving and rotating the fundus image relative to the eyeball data through image processing, the control unit 70 performs a matching process so that a three-dimensional correlativity is increased between the three-dimensional shape of the fundus in the eyeball data and the three-dimensional shape of the fundus in the fundus data. The surface shape of the fundus or a retinal layer, for example, is used as reference data of the matching process.

The control unit 70 adjusts a positional relationship between a yellow spot center in the eyeball data and a yellow spot center in the fundus data. Next, the control unit 70 moves the tomographic images in traverse directions constituting the three-dimensional data of the fundus (B scan images) in the Z direction through image processing so as to follow the three-dimensional shape of the eyeball data. Accordingly, any positional shift between the tomographic images constituting the fundus data is corrected so that the three-dimensional data of the fundus can be accurately obtained.

<Modified Embodiment 1>

Alternatively, any relative positional shift between the tomographic images may be corrected through image processing based on front images corresponding to the tomographic images (tomographic images of the anterior segment and the fundus) used as template images.

For example, the amount and direction of any positional shift between the front image of the anterior segment obtained at substantially the same time as the three-dimensional tomographic image of the anterior segment (may be obtained at exactly the same time) and the front image of the anterior segment obtained at substantially the same time as the three-dimensional tomographic image of the fundus are detected through image processing. Then, the positional shift between the tomographic image of the anterior segment and the tomographic image of the fundus is corrected based on the detected positional shift.

Alternatively, a positional shift may be detected between the front image of the anterior segment obtained based on the data constituting the three-dimensional tomographic image of the anterior segment (for example, integrated image in the depth direction of the tomographic images, integrated value of the spectrum data at X-Y positions) and the front image of the anterior segment obtained at substantially the same time as the three-dimensional tomographic image of the fundus.

As to a positional relationship between the images of the anterior segment and the fundus in the Z direction, an ocular axial length of the eye E is used. A sensor which detects a relative position of the apparatus to the eye E in the Z direction (for example, a light enters the eye E in an oblique direction and a reflected light is obtained in an opposite direction to detect the Z position) is provided, and a detection result is obtained at substantially the same timing as obtaining the tomographic image. Then, any positional shift in the Z direction can be corrected.

The positional shift correction is not necessarily limited to the method described so far. The front image of a site of the eye corresponding to the tomographic image (image of the anterior segment or the fundus) may be used to correct any positional shift between the tomographic images. For example, the front image of the fundus corresponding to the tomographic image may be used, both the front images of the anterior segment and the fundus corresponding to the tomographic image may be used, or the front image of the intermediate segment may be used.

<Modified Embodiment 2>

The control unit 70 may change an imaging region of the tomographic image in the depth direction by changing the optical path difference between the measurement light and the reference light in a predetermined step to thereby sequentially obtain the three-dimensional tomographic images of the region of the eye E from the cornea through the fundus. The tomographic images sequentially obtained are synthesized so that the three-dimensional tomographic image showing the general view of the eye E is obtained. As a result, information of the three-dimensional shapes of the region from the cornea through the retina (including anterior chamber depth, ocular axial length) can be obtained. Further, the tomographic image of the intermediate light-transmittable segment situated between the anterior segment and the fundus can also be obtained. Whenever the imaging region is changed, the focal point of the measurement light emitted from the light-guiding optical system 504 is changed.

<Modified Embodiment 3>

In the description given so far, the three-dimensional tomographic image of the fundus and the three-dimensional tomographic image of the anterior segment are obtained to construct the tomographic image of the eye. However, the apparatus according to the present invention is not necessarily limited thereto as far as the apparatus is provided with a first tomography imaging device configured to irradiate the measurement light on a first site of the eye E to obtain a first three-dimensional tomographic image by the optical coherence tomography, a second tomography imaging device configured to irradiate the measurement light on a second site of the eye E to obtain a second three-dimensional tomographic image by the optical coherence tomography, an image processing device configured to construct a three-dimensional tomographic image in a broader range through image processing based on the first and second three-dimensional tomographic images, and an output device configured to output the three-dimensional tomographic image in the broader range obtained by the image processing device.

For example, the first site may be the anterior segment and the second site may be the intermediate segment, or the first site may be a center portion of the fundus and the second site may be a peripheral portion of the fundus. In the apparatus thus configured, any positional shift between the first and second three-dimensional tomographic images is corrected.

In the description given so far, the imaging range in the depth direction is set on the whole eye, and the tomographic image of the whole eye including the cornea through the fundus is obtained by the optical coherence tomography. However, the apparatus according to the present invention is not necessarily limited thereto as far as the apparatus is provided with a large-depth imaging device wherein the imaging range in the depth direction is set in a large depth, and a large-depth tomographic image is obtained by the optical coherence tomography. The image processing device associates the first three-dimensional tomographic image obtained by the first tomography imaging device and the second three-dimensional tomographic image obtained by the second tomography imaging device with the large-depth tomographic image obtained by the large-depth imaging device. hi the apparatus thus configured, the large-depth imaging device is preset to have an imaging range larger than the imaging ranges of the first and second three-dimensional tomographic images.

DESCRIPTION OF THE REFERENCE SIGNS

12 Fundus tomography imaging device
14 Anterior segment tomography imaging device
16 Eye distance measuring device
18 Processor
22 Monitor
28 Another device
200 OCT optical system

What is claimed is:

1. A method of observing a tomographic image of an examinee's eye to be examined, including:
    obtaining a first tomographic image which is a tomographic image of an anterior segment of the examinee's eye by an optical coherence tomography optical system for obtaining a tomographic image by guiding a measurement light to the anterior segment of the examinee's eye;
    obtaining a second tomographic image which is a tomographic image of a fundus of the examinee's eye by optical coherence tomography optical system for obtaining a tomographic image by guiding the measurement light to the fundus of the examinee's eye by a timing different from a timing of obtaining the first tomographic image;
    constructing a tomographic eyeball image of the examinee's eye based on the obtained first and second tomographic images; and
    displaying the constructed tomographic eyeball image on a monitor.

2. The method according to claim 1, wherein
    the obtained tomographic images are analyzed through image processing, and
    a part of the eyeball image corresponding to a site of the examinee's eye where an abnormality is detected by the analysis is displayed on the monitor in a highlighted manner.

3. The method according to claim 1, wherein
    an analysis for detecting a predefined eye disorder is performed to both the first and second tomographic images,
    an analysis result of the first tomographic image and an analysis result of the second tomographic image are subjected to an integrated analysis, and
    a result of the integrated analysis is displayed on the monitor.

4. The method according to claim 1, wherein
    the first tomographic image is processed to analyze thicknesses of layers of the fundus and the second tomographic image is processed to analyze an opening degree of gonioangle in order to perform an analysis for detecting glaucoma,
    the thicknesses of the layers of the fundus and the opening degree of gonioangle are subjected to an integrated analysis, and
    a result of the integrated analysis is displayed on the monitor.

5. The method according to claim 4, wherein
    a part of the tomographic eyeball image corresponding to a site of the examinee's eye where an abnormality is detected by the analysis is displayed on the monitor in a highlighted manner.

6. The method according to claim 1, wherein
    a tomographic image of the examinee's eye obtained by a technique different from the optical coherence tomography optical system is synthesized with the tomographic eyeball image.

7. The method according to claim 1, wherein
    a distance between the first and second tomographic images constituting the tomographic eyeball image is set based on information of a distance between the anterior segment and the fundus measured by an eye distance measuring device.

8. The method according to claim 1, wherein
    a tomographic image of a whole eye including a region from a cornea through the fundus is obtained by the optical coherence tomography optical system having an imaging range from the cornea through the fundus, and
    an anterior segment region in the obtained tomographic image of the whole eye and the first tomographic image are subjected to a matching process, and the fundus region in the obtained tomographic image of the whole eye and the second tomographic image are subjected to a matching process.

9. The method according to claim 8, wherein
    the optical coherence tomography optical system is a swept source optical coherence tomography optical system having a wavelength-variable light source,
    a wavelength width of a light emitted from the wavelength-variable light source and the number of sampling points in the wavelength width are set so that the whole eye including the region from the cornea through the fundus is included in an imaging range in a depth direction when the tomographic image of the whole eye is obtained, and
    the wavelength width of the light emitted from the wavelength-variable light source and the number of sampling points in the wavelength width are set so that the imaging range in the depth direction corresponds to respective sites of the examinee's eye when the first and second tomographic images are obtained.

10. The method according to claim 1, wherein
    a positional shift of a tomographic image of the whole eye is corrected by image processing so that a shape of a corneal surface is equal to a shape of the corneal surface obtained by a corneal topography.

11. The method according to claim 1, wherein
optical information of the examinee's eye and optical information of an intraocular lens, and a simulation of an intraocular lens operation is performed, and
a graphic representing the intraocular lens is synthesized with an anterior segment region of the outputted tomographic eyeball image.

12. The method according to claim 11, wherein
a prospective postoperative outcome depending on a location of the intraocular lens.

13. A method of observing a tomographic image of an examinee's eye to be examined, including:
obtaining a tomographic image of a whole eye including a region from a cornea through a fundus by an optical coherence tomography optical system having an imaging range from the cornea through the fundus; and
performing at least one of
a matching process of an anterior segment region in the obtained tomographic image of the whole eye and a first tomographic image which is a tomographic image of an anterior segment of the examinee's eye obtained by the optical coherence tomography optical system, and
a matching process of the fundus region in the obtained tomographic image of the whole eye and a second tomographic image which is a tomographic image of the fundus of the examinee's eye obtained by the optical coherence tomography optical system by a timing different from a timing of obtaining the first tomographic image.

14. The method according to claim 13, wherein
the optical coherence tomography optical system is a swept source optical coherence tomography optical system having a wavelength-variable light source,
a wavelength width of a light emitted from the wavelength-variable light source and the number of sampling points in the wavelength width are set so that the whole eye including the region from the cornea through the fundus is included in the imaging range in a depth direction when the tomographic image of the whole eye is obtained, and
the wavelength width of the light emitted from the wavelength-variable light source and the number of sampling points in the wavelength width are set so that the imaging range in the depth direction corresponds to respective sites of the examinee's eye when the first and second tomographic images are obtained.

* * * * *